United States Patent [19]
Lesher et al.

[11] 4,297,363
[45] Oct. 27, 1981

[54] 2-AMINO-3(4 OR 5)-(PYRIDINYL)PHENOLS AND THEIR USE AS CARDIOTONICS

[75] Inventors: George Y. Lesher, Shodack; Baldev Singh, East Greenbush, both of N.Y.

[73] Assignee: Sterling Drug Inc., New York, N.Y.

[21] Appl. No.: 170,896

[22] Filed: Jul. 21, 1980

[51] Int. Cl.³ .................. C07D 213/30; A61K 31/44
[52] U.S. Cl. ..................................... 424/263; 546/334
[58] Field of Search .......................... 546/334; 424/263

[56]     References Cited
U.S. PATENT DOCUMENTS 3,753,993  8/1973  Lesher et al. ................... 424/258 X
3,907,808  9/1975  Lesher et al. ................... 424/258 X

OTHER PUBLICATIONS

Heilbron, et al, J. Chem. Soc., 1940, pp. 1279–1284.

Coates, et al., J. Chem. Soc., 1943, pp. 406–413.

Primary Examiner—Joseph Paul Brust
Attorney, Agent, or Firm—Robert K. Bair; B. Woodrow Wyatt

[57]     ABSTRACT

2-Amino-3(4 or 5)-PY-phenol, a cardiotonic agent, is prepared by reducing 2-nitro-3(4 or 5)-PY-phenol, where PY is 4- or 3-pyridinyl or 4- or 3-pyridinyl having one or two lower-alkyl substituents. 2-Amino-3(4 or 5)-PY-phenol or pharmaceutically-acceptable acid-addition salt thereof is disclosed as the active component in a cardiotonic composition for increasing cardiac contractility and in the method for increasing cardiac contractility in a patient requiring such treatment. The novel isomeric 4-amino-5-(4-pyridinyl)phenol is shown for comparative purposes.

12 Claims, No Drawings

2-AMINO-3(4 OR 5)-(PYRIDINYL)PHENOLS AND THEIR USE AS CARDIOTONICS

BACKGROUND OF THE INVENTION

CROSS-REFERENCE TO RELATED APPLICATION

3(or 4)-PY-benzenamines and selected acyl derivatives, the former used herein as intermediates, are disclosed and claimed as cardiotonic agents in copending application Ser. No. 152,991, filed May 27, 1980.

(a) Field of the Invention

This invention relates to (pyridinyl)-aminophenols, their preparation and their use as cardiotonics.

(b) Description of the Prior Art

Coates et al [J. Chem. Soc. 1943, 406] show the preparation of 4-(2-pyridinyl)-2-aminophenol in four steps from N-acetyl-4-(2-pyridinyl)aniline, the last two steps comprising converting 2-nitro-4-(2-pyridinyl)aniline to 2-nitro-4-(2-pyridinyl)phenol and reducing the latter to convert nitro to amino. Coates et al also show 3-(4-pyridinyl)phenol, an compound used as an intermediate herein. Coates utilized said pyridinyl-phenols as intermediates to prepare pyridinyl-quinolines, which in turn were investigated for possible spasmolytic activity with disappointing results.

Heilbron et al [J. Chem. Soc. 1940, 1279] show as intermediates in the preparation of 3- and 4-pyridyl-diphenyls the following compounds: β-3-aminophenyl-pyridine, β-4-aminophenylpyridine and ν-4-aminophenylpyridine and the N-acetyl derivatives of each, including the hydrochloride salt of β-4-acetamidophenylpyridine; these three aminophenylpyridines currently are named 3-(3-pyridinyl)benzeneamine, 4-(3-pyridinyl)benzeneamine and 4-(4-pyridinyl)benzeneamine, respectively, used as intermediates herein.

Lesher and Carabateas [U.S. Pat. Nos. 3,753,993 (8-21-73) and 3,907,808 (9-23-75)] show as intermediates for making quinoline antibacterial agents various 3-(substituted-pyridinyl)benzeneamines where pyridinyl is substituted, inter alia, by lower-alkyl, illustrated by, 3-(2-methyl-4-pyridinyl)benzeneamine, 3-(2,6-dimethyl-4-pyridinyl)benzeneamine, 3-(2,6-diethyl-4-pyridinyl)-benzeneamine, 3-(2,5-dimethyl-4-pyridinyl)benzeneamine, 3-(3-methyl-4-pyridinyl)benzeneamine, 3-(2-ethyl-4-pyridinyl)benzeneamine, and 3-(2,3-dimethyl-4-pyridinyl)benzeneamine, which are used as intermediates herein.

SUMMARY OF THE INVENTION

In a composition of matter aspect, the invention resides in the compound 2-amino-3(4 or 5)-[4(or 3)-pyridinyl]phenol or salt thereof, useful as a cardiotonic agent.

In a process aspect, the invention comprises reducing 2-nitro-3(4 or 5)-[4(or 3)-pyridinyl]phenol to produce 2-amino-3-(4 or 5)-[4(or 3)-pyridinyl]phenol.

In a composition aspect, the invention relates to a cardiotonic composition for increasing cardiac contractility, said composition comprising a pharmaceutically-acceptable carrier and, as the active component thereof, the cardiotonic 2-amino-3(4 or 5)-pyridinyl)phenol or salt.

In a method aspect, the invention relates to a method for increasing cardiac contractility in a patient requiring such treatment which comprises administering to such patient an effective amount of a cardiotonic 2-amino-3(4 or 5)-(pyridinyl)phenol or salt.

DETAILED DESCRIPTION INCLUSIVE OF PREFERRED EMBODIMENTS

In a composition of matter aspect, the invention resides in 2-amino-3(4 or 5)-PY-phenol or pharmaceutically-acceptable acid-addition salt thereof, where PY is 4- or 3-pyridinyl or 4-or 3-pyridinyl having one or two lower-alkyl substituents.

In a process aspect, the invention resides in the process which comprises reacting 2-nitro-3(4 or 5)-PY-phenol with a reducing agent capable of converting nitro to amino to produce 2-amino-3(4 or 5)-PY-phenol, where PY is 4- or 3-pyridinyl or 4-or 3-pyridinyl having one or two lower-alkyl substituents.

A composition aspect of the invention resides in the cardiotonic composition for increasing cardiac contractility, said composition which comprises a pharmaceutically-acceptable pharmaceutical carrier and, as the active component thereof, an effective amount of the cardiotonic 2-amino-3(4 or 5)-PY-phenol or pharmaceutically-acceptable acid-addition salt thereof, where PY is 4- or 3-pyridinyl or 4- or 3-pyridinyl having one or two lower-alkyl substituents. Preferred embodiments of this aspect of the invention are the compositions having, as the active component, said compound where PY is 4- or 3-pyridinyl or said salt thereof.

A method aspect of the invention resides in the method for increasing cardiac contractility in a patient requiring such treatment which comprises administering to such patient an effective amount of the cardiotonic 2-amino-3(4 or 5)-PY-phenol or pharmaceutically-acceptable salt thereof, where PY is 4- or 3-pyridinyl or 4- or 3-pyridinyl having one or two lower-alkyl substitutents, a preferred embodiment being the method using said compound where PY is 4- or 3-pyridinyl.

The term "lower-alkyl" as used herein, e.g., as the meaning of the substituent for PY means alkyl radicals having from 1 to 6 carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

Illustrative of PY where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The 2-amino-3(4 or 5)-PY-phenol is useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the hydrochloride or lactate. However, other appropriate pharmaceutically-acceptable salts within the scope of the invention are those derived from mineral acids such as hydrobromic acid, sulfuric acid, phosphoric acid and sulfamic acid; and organic acid such as acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of 2-amino-3(4 or 5)-PY-phenol was assigned on the basis of evidence provided by infrared, ultraviolet, nuclear magnetic resonance and mass spectra, by chromatographic mobilities, by the correspondence of calculated and found values for the elemental analyses, and, by its method of preparation.

The manner of making and using the instant invention will now be generally described so as to enable a person skilled in the art of pharmaceutical chemistry to make and use the same, as follows.

The reaction of 2-nitro-3(4 or 5)-PY-phenol with a reducing agent or produce 2-amino-3(4 or 5)-PY-phenol was conveniently carried out either by catalytic or chemical reductive means. In practicing the invention, this reduction was conveniently run in a suitable solvent, e.g., acetic acid, dimethylformamide, in the presence of a hydrogenation catalyst, e.g., platinum oxide, palladium-on-charcoal, under catalytic hydrogenation conditions at ambient temperature (about 20° to 25° C.) until the uptake of hydrogen ceased. Other suitable solvents include tetrahydrofuran, dioxane, methanol, ethanol, water (containing a base, e.g., sodium hydroxide, potassium hydroxide, triethylamine, etc.), and the like. Other suitable hydrogenation catalysts include Raney nickel, and the like. Chemical reducing agents useful in the reduction of the 2-nitro compound to produce the 2-amino compound include iron and acetic acid, zinc and hydrochloric acid, and the like.

The intermediate 2-nitro-3(4 or 5)-PY-phenols are prepared by nitrating the generally known 3(or 4)-PY-phenols by conventional nitrating procedures, as illustrated hereinbelow in Examples B-1 through B-20.

The generally known 3(or 4)-PY-phenols are conveniently prepared by the generally known procedure of converting corresponding 3(or 4)-PY-benzenamines via aqueous hydrolysis of their diazonium salts.

The following examples will further illustrate the invention without, however, limiting it thereto.

A. 3(4 or 5)-PY-PHENOLS

These intermediates, which include novel as well as known compounds, are prepared by the generally known procedure of converting the corresponding generally known 3(4 or 5)-PY-benzeneamine to its diazonium salt and then converting the salt to the desired 3(4 or 5)-PY-phenol, as illustrated below in Examples A-1 through A-11.

A-1. 4-(4-Pyridinyl)phenol—To an ice cold stirred mixture containing 85 g. of 4-(4-pyridinyl)benzeneamine, 250 ml. of concentrated sulfuric acid and 1 liter of water was added with stirring over a period of 2 hours a solution containing 35 g. of sodium nitrate in 100 ml. of water, keeping the reaction temperature below 5° C. during the addition. The resulting dark solution was left room temperature overnight and then filtered. The filtrate was heated on a steam bath for 4 hours, treated with decolorizing charcoal and filtered. The filtrate was chilled in an ice bath and was neutralized by adding concentrated ammonium hydroxide. The resulting yellow precipitate was collected, washed with water and dried at 80° C. to yield 75.8 g. of 4-(4-pyridinyl)pheneol, m.p. 240°–244° C.

A-2. 3-(4-Pyridinyl)phenol, 242.4 g., m.p. 223°–224° C., [Coates et al, J. Chem. Soc. 1943, 406 (411), m.p. 227°–228° C.], was obtained following the procedure described in Example A-1 using 255 g. of 3-(4-pyridinyl)benzeneamine, 400 ml. of concentrated sulfuric acid, 2 liters of water and 104 g. of sodium nitrate in 250 ml. of water, the latter added over a period of 100 minutes.

Following the procedure described in Example A-1 but using a molar equivalent quantity of the appropriate 3(or 4)-PY-benzeneamine in place of 4-(4-pyridinyl)benzeneamine, it is contemplated that the corresponding 3(or 4)-PY-phenols of Examples A-3 thru A-11 can be obtained.

A-3. 4-(3-Pyridinyl)phenol, using 4-(3-pyridinyl)benzeneamine.

A-4. 3-(2-Methyl-4-pyridinyl)phenol, using 3-(2-methyl-4-pyridinyl)benzeneamine.

A-5. 3-(2,6-Dimethyl-4-pyridinyl)phenol, using 3-(2,6-dimethyl-4-pyridinyl)benzeneamine.

A-6. 3-(2,6-Diethyl-4-pyridinyl)phenol, using 3-(2,6-diethyl-4-pyridinyl)benzeneamine.

A-7. 3-(2,5-Dimethyl-4-pyridinyl)phenol, using 3-(2,5-dimethyl-4-pyridinyl)benzeneamine.

A-8. 3-(2,3-Dimethyl-4-pyridinyl)phenol, using 3-(2,3-dimethyl-4-pyridinyl)benzeneamine.

A-9. 3-(3-Methyl-4-pyridinyl)phenol, using 3-(3-methyl-4-pyridinyl)benzeneamine.

A-10. 3-(2-Ethyl-4-pyridinyl)phenol, using 3-(2-ethyl-4-pyridinyl)benzeneamine.

A-11. 3-(3-Pyridinyl)phenol, using 3-(3-pyridinyl)benzeneamine.

B. 2-NITRO-3(4 or 5)-PY-PHENOLS

B-1. 2-Nitro-4-(4-pyridinyl)phenol—To a stirred mixture containing 51.3 g. of 4-(4-pyridinyl)phenol and 500 ml. of acetic acid cooled in an ice cold water bath was added over 20 minute period a solution containing 15 ml. of concentrated nitric acid in 50 ml. of acetic acid. The resulting mixture was heated gently with stirring on a steam bath for 4 hours and then allowed to stand at ambient temperature over the weekend the resulting reaction mixture was heated in vacuo to distill off about 400 ml. of acetic acid. To the residue was added 300 ml. of water and 75 ml. of concentrated ammonium hydroxide. The solid that separated was collected, washed with water and dried at 80° C. to yield 61.2 g. of 2-nitro-4-(4-pyridinyl)phenol, m.p. 210°–212° C.

B-2. 2-Nitro-5-(4-pyridinyl)phenol—This compound along with two other isomers, namely, 4-nitro-3-(4-pyridinyl)phenol and 2-nitro-3-(4-pyridinyl)phenol (Example B-3), were all obtained when 3-(4-pyridinyl)phenol was nitrated as in Example B-1. To an ice cold mixture of 242 g. of 3-(4-pyridinyl)phenol and 1 liter of glacial acetic acid was added with stirring a solution containing 60 ml. of concentrated nitric acid in 200 ml. of glacial acetic acid over a 40 minutes period, maintaining the reaction temperature between 10°–15° C. The reaction mixture was stirred at room temperature for 1 hour, next gently heated on a steam bath for 4 hours and then allowed to stand at ambient temperature for 16 hours. The reaction mixture was concentrated on a rotary evaporator to remove about 700 ml. of acetic acid. The resulting slurry was poured into 1 liter of water and was neutralized by adding aqueous ammonium hydroxide. The resulting solid was collected, washed with water and dried at 80° C. It was crystallized from acetic acid (2 l.), collected and dried at 80° C. to produce 50.4 g. of 4-nitro-3-(4-pyridinyl)phenol, m.p. >300° C. The mother liquor was concentrated to give another 34 g. of crude 4-nitro-3-(4-pyridinyl)phenol.

The resulting mother liquor after removal of the 34 g. of 4-nitro isomer was concentrated to dryness. The residue was dissolved in 2 liters of boiling ethanol and filtered to remove a small quantity (4 g.) of insoluble material. The filtrate was concentrated to a volume of about 1 liter and allowed to cool. The crystalline precipitate was collected and dried at 80° C. to yield 64 g. of 2-nitro-5-(4-pyridinyl)phenol, m.p. 174°–176° C.

The filtrate, which contained the third isomer, was worked up as described in Example B-3.

B-3. 2-Nitro-3-(4-pyridinyl)phenol—The filtrate referred to in the last paragraph of Example B-2 was concentrated to dryness to yield 67.2 of a yellow solid whose nmr spectrum indicated it to be a mixture of mostly 4-nitro-3-(4-pyridinyl)phenol and small quantities of 2-nitro-3-(4-pyridinyl)phenol and 2-nitro-5-(4-pyridinyl)phenol. This mixture was used in Example C-3 hereinbelow.

Following the procedure described in Example B-1, B-2 or B-3 but using a molar equivalent quantitiy of the appropriate 3(or 4)-PY-phenol in place of 4-(4-pyridinyl)phenol or 3-(4-pyridinyl)phenol, respectively, it is contemplated that the corresponding 2-nitro-3(4 or 5)-PY-phenols of Examples B-4 thru B-20 can be obtained.

B-4. 2-Nitro-4-(3-pyridinyl)phenol, using 4-(3-pyridinyl)phenol.

B-5. and B-6. 2-Nitro-5-(2-methyl-4-pyridinyl)phenol and 2-Nitro-3-(2-methyl-4-pyridinyl)phenol, using 3-(2-methyl-4-pyridinyl)phenol.

B-7. and B-8. 2-Nitro-5-(2,6-dimethyl-4-pyridinyl)phenol and 2-Nitro-3-(2,6-dimethyl-4-pyridinyl)phenol, using 3-(2,6-dimethyl-4-pyridinyl)phenol.

B-9. and B-10. 2-Nitro-5-(2,6-diethyl-4-pyridinyl)phenol and 2-Nitro-3-(2,6-diethyl-4-pyridinyl)phenol, using 3-(2,6-diethyl-4-pyridinyl)phenol.

B-11. and B-12. 2-Nitro-5-(2,5-dimethyl-4-pyridinyl)phenol and 2-Nitro-3-(2,5-dimethyl-4-pyridinyl)phenol, using 3-(2,5-dimethyl-4-pyridinyl)phenol.

B-13. and B-14. 2-Nitro-5-(2,3-dimethyl-4-pyridinyl)phenol and 2-Nitro-3-(2,3-dimethyl-4-pyridinyl)phenol, using 3-(2,3-dimethyl-4-pyridinyl)phenol.

B-15. and B-16. 2-Nitro-5-(3-methyl-4-pyridinyl)phenol and 2-Nitro-3-(3-methyl-4-pyridinyl)phenol, using 3-(3-methyl-4-pyridinyl)phenol.

B-17. and B-18. 2-Nitro-5-(2-ethyl-4-pyridinyl)phenol and 2-Nitro-3-(2-ethyl-4-pyridinyl)phenol, using 3-(2-ethyl-4-pyridinyl)phenol.

B-19. and B-20. 2-Nitro-5-(3-pyridinyl)phenol and 2-Nitro-3-(3-pyridinyl)phenol, using 3-(3-pyridinyl)phenol.

C. 2-AMINO-3(4 or 5)-PY-PHENOLS

C-1. 2-Amino-4-(4-pyridinyl)phenol—A mixture containing 21.6 g. of 2-nitro-4-(4-pyridinyl)phenol, 175 ml. of acetic acid, 25 ml. of water and 1 g. of platinum dioxide was shaken with hydrogen under catalytic hydrogenation conditions until the required amount of hydrogen was taken up. The catalyst was filtered off and to the filtrate was added 100 ml. of concentrated hydrochloric acid and the mixture heated in vacuo to dryness. The residue was stirred with methanol and the product collected, dried at 90° C. to yield 22.4 g. of 2-amino-4-(4-pyridinyl)phenol as its dihydrochloride, m.p. >300° C.

Other acid-addition salts of 2-amino-4-(4-pyridinyl)phenol are conveniently prepared by adding to a mixture of 1 g. of 2-amino-4-(4-pyridinyl)phenol in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring a molar equivalent quantity each of 2-amino-4-(4-pyridinyl)phenol and the appropriate acid, e.g., lactic acid or hydrochloric acid, to prepare respectively the lactate or hydrochloride salt of 2-amino-4-(4-pyridinyl)phenol in aqueous solution.

C-2. 2-Amino-5-(4-pyridinyl)phenol—A mixture containing 47 g. of 2-nitro-5-(4-pyridinyl)phenol, 1.2 g. of 10% palladium-on-charcoal and 200 ml. of dimethylformamide was shaken under catalytic hydrogenation conditions until the required quantity of hydrogen was taken up. The catalyst was filtered off and the filtrate was treated with decolorizing charcoal and then evaporated to dryness in vacuo. The residue was digested with 300 ml. of ethanol and then allowed to stand at room temperature for 4 hours. The product was collected, washed well with ethanol and dried at 90° C. to yield 21.2 g. of 2-amino-5-(4-pyridinyl)phenol, m.p. 212°–215° C. with decomposition.

Acid-addition salts of 2-amino-5-(4-pyridinyl)phenol are conveniently prepared by adding to a mixture of 1 g. of 2-amino-5-(4-pyridinyl)phenol in about 20 ml. of aqueous methanol the appropriate acid, e.g., hydrochloride, methanesulfonic acid, concentrated sulfuric acid, concentrated phosphoric acid, to a pH of about 2 to 3, chilling the mixture after partial evaporation and collecting the precipitated salt, e.g., dihydrochloride, dimethanesulfonate, sulfate, phosphate, respectively.

Also, the acid-addition salt is conveniently prepared in aqueous solution by adding to water with stirring a molar equivalent quantity each of 2-amino-5-(4-pyridinyl)phenol and the appropriate acid, e.g., lactic acid or hydrochloric acid, to prepare respectively the lactate or hydrochloride salt of 2-amino-5-(4-pyridinyl)phenol in aqueous solution.

C-3. 2-Amino-3-(4-pyridinyl)phenol—A 21.6 g. portion of the 67.2 g. mixture of the three isomeric 2-nitro-3-(4-pyridinyl)phenol, 4-nitro-3-(4-pyridinyl)phenol and 2-nitro-5-(4-pyridinyl)phenol from Example B-3 above was mixed with 200 ml. of dimethylformamide and 1 g. of 10% palladium-on-charcoal; and, the mixture was shaken under hydrogen under catalytic hydrogenation conditions until the required amount of hydrogen was taken up. The catalyst was filtered off and the filtrate was evaporated to dryness. The remaining 45.6 g. portion of said 67.2 mixture of three isomers was reduced in the same manner and the combined residues were recrystallized from methanol to yield 30.2 g. of 4-amino-3-(4-pyridinyl)phenol, m.p., 213°–215° C. with decomposition. The residue (about 20 g.) obtained by evaporation of the methanolic mother liquor was separated by chromatography using 600 g. of a silica gel column in a 1 liter sintered glass Buchner funnel, and 15 liters of 3% methanol in ether as the eluent, thereby obtaining 11.2 g. more of 4-amino-3-(4-pyridinyl)phenol and, after recrystallization from ethanol, 6.5 g. of 2-amino-3-(4-pyridinyl)phenol m.p., 283°–285° c. with decomposition.

Acid-addition salts of 2-amino-3-(4-pyridinyl)phenol are conveniently prepared by adding to a mixture of 1 g. of 2-amino-3-(4-pyridinyl)phenol in about 20 ml. of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., dihydrochloride, dimethanesulfonate, sulfate, phosphate, respectively. Also, the acid-addition salt is conveniently prepared in aqueous solution by adding to water with stirring a molar equivalent quantity each of 2-amino-3-(4-pyridinyl)phenol and the appropriate acid, e.g., lactic acid or hydrochloric acid, to prepare respectively the lactate or hydrochloride salt of 2-amino-3-(4-pyridinyl)phenol in aqueous solution.

Following the procedures described in Example C-2 but using a molar equivalent quantity of the appropriate 2-nitro-3(4 or 5)-PY-phenols in place of 2-nitro-5-(4-pyridinyl)phenol, it is contemplated that the corresponding 2-amino-3-(4 or 5)-PY-phenols of Examples C-4 thru C-20 can be obtained.

C-4. 2-Amino-4-(3-pyridinyl)phenol
C-5. 2-Amino-5-(2-methyl-4-pyridinyl)phenol
C-6. 2-Amino-3-(2-methyl-4-pyridinyl)phenol
C-7. 2-Amino-5-(2,6-dimethyl-4-pyridinyl)phenol
C-8. 2-Amino-3-(2,6-dimethyl-4-pyridinyl)phenol
C-9. 2-Amino-5-(2,6-dimethyl-4-pyridinyl)phenol
C-10. 2-Amino-3-(2,6-diethyl-4-pyridinyl)phenol
C-11. 2-Amino-5-(2,5-dimethyl-4-pyridinyl)phenol
C-12. 2-Amino-3-(2,5-dimethyl-4-pyridinyl)phenol
C-13. 2-Amino-5-(2,3-dimethyl-4-pyridinyl)phenol
C-14. 2-Amino-3-(2,3-dimethyl-4-pyridinyl)phenol
C-15. 2-Amino-5-(3-methyl-4-pyridinyl)phenol
C-16. 2-Amino-3-(3-methyl-4-pyridinyl)phenol
C-17. 2-Amino-5-(2-ethyl-4-pyridinyl)phenol
C-18. 2-Amino-3-(2-ethyl-4-pyridinyl)phenol
C-19. 2-Amino-5-(3-pyridinyl)phenol
C-20. 2-Amino-3-(3-pyridinyl)phenol The compound of C-21 shown hereinbelow is outside the scope of the instant invention and is presented here primarily for comparative purposes.

C-21. 4-Amino-3-(4-pyridinyl)phenol, 11.5 g., 212°–214° C. was prepared following the procedure described in Example C-2 using 16 g. of 4-nitro-3-(4-pyridinyl)phenol, 1 g. of 10% palladium-on-charcoal and 200 ml. of dimethylformamide.

The usefulness of 2-amino-3(4 or 5)-PY-phenol or salt as cardiotonic agent is demonstrated by its effectiveness in standard pharmacological test procedures, for example, in causing a significant increase in the contractile force of the isolated cat atria and papillary muscle. This test procedure is described U.S. Pat. No. 4,072,746, issued Feb. 7, 1978.

When tested by the above-described isolated cat atria and papillary muscle procedure, 2-amino-3(4 or 5)-PY-phenol or salt at doses of 30, 100 or 300 µg./ml. was found to cause a significant increase, that is, greater than 25%, in papillary muscle force and a significant increase, that is, greater than 25%, in right artrial force, while causing a lower percentage increase (than that of papillary muscle force and right atrial force) in right atrial rate. In contrast, the isomeric novel 4-amino-3-(4-pyridinyl)phenol (Example C-21) was found to be inactive at doses of 30 and 100 µg./ml. in the same cat atria test. A preferred embodiment, namely, 2-amino-4-(4-pyridinyl)phenol or salt thereof, e.g., dihydrochloride, was found to cause 115% and 191% increases in papillary muscle force at 30 and 100 µg./ml., respectively, and to cause 43% and 85% increases in right atrial force at the same respective doses.

The present invention includes within its scope a cardiotonic composition for increasing cardiac contractility, said composition comprising a pharmaceutically-acceptable carrier and, as the active component thereof, the cardiotonic 2-amino-3(4 or 5)-PY-phenol or pharmaceutically-acceptable acid-addition salt thereof. The invention also includes within its scope the method for increasing cardiac contractility in a patient requiring such treatment which comprises administering to such patient an effective amount of said 2-amino-3(4 or 5)-PY-phenol or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all critieria and utilizing his best judgement on the patient's behalf.

We claim:

1. 2-Amino-3(4 or 5)-PY-phenol or pharmaceutically-acceptable acid-addition salt thereof, where PY is 4- or 3-pyridinyl or 4- or 3-pyridinyl having one or two lower-alkyl substituents.

2. 2-Amino-3-(4-pyridinyl)phenol or pharmaceutically-acceptable acid-addition salt thereof.

3. 2-Amino-4-(4-pyridinyl)phenol or pharmaceutically-acceptable acid-addition salt thereof.

4. 2-Amino-5-(4-pyridinyl)phenol or pharmaceutically-acceptable acid-addition salt thereof.

5. A cardiotonic composition for increasing cardiac contractility, said composition comprising a pharmaceutically-acceptable inert carrier and, as the active component thereof, a cardiatonically-effective amount of 2-amino-3(4 or 5)-PY-phenol or pharmaceutically-acceptable acid-addition salt thereof, where PY is 4- or 3-pyridinyl or 4- or 3-pyridinyl having one or two lower-alkyl substituents.

6. A composition according to claim 5 wherein the active component is 2-amino-3-(4-pyridinyl)phenol or pharmaceutically-acceptable salt thereof.

7. A composition according to claim 5 where the active component is 2-amino-4-(4-pyridinyl)phenol or pharmaceutically-acceptable salt thereof.

8. A composition according to claim 5 where the active component is 2-amino-5-(4-pyridinyl)phenol or pharmaceutically-acceptable salt thereof.

9. The method for increasing cardiac contractility in a patient requiring such treatment which comprises administering orally or parenterally in a solid or liquid dosage form to such patient a cardiotonically-effective amount of 2-amino-3(4 or 5)-PY-phenol or pharmaceutically-acceptable acid-addition salt thereof, where PY is 4- or 3-pyridinyl or 4- or 3-pyridinyl having one or two lower-alkyl substituents.

10. The method according to claim 9 where the cardiotonic is 2-amino-3-(4-pyridinyl)phenol or pharmaceutically-acceptable acid-addition salt thereof.

11. The method according to claim 9 where the cardiotonic is 2-amino-4-(4-pyridinyl)phenol or pharmaceutically-acceptable acid-addition salt thereof.

12. The method according to claim 9 where the cardiotonic is 2-amino-5-(4-pyridinyl)phenol or pharmaceutically-acceptable acid-addition salt thereof.

* * * * *

UNITED STATES PATENT AND TRADEMARK OFFICE
CERTIFICATE OF CORRECTION

PATENT NO. : 4,297,363
DATED : October 27, 1981
INVENTOR(S) : George Y. Lesher and Baldev Singh It is certified that error appears in the above-identified patent and that said Letters Patent are hereby corrected as shown below:

Column 1, line 31, "$\gamma$" should read -- Y --.

Column 1, line 58, "2-amino-3-(4 or 5)" should read -- 2-amino-3(4 or 5) --.

Column 3, line 41, "or" should read -- to --.

Column 10, claim 5, line 8, "cardiatonically" should read -- cardiotonically --.

Column 10, claim 6, line 13, "wherein" should read -- where --.

Signed and Sealed this

Eighth Day of June 1982

[SEAL]

Attest:

Attesting Officer

GERALD J. MOSSINGHOFF

Commissioner of Patents and Trademarks